United States Patent [19]

Suzuki et al.

[11] Patent Number: 5,072,036

[45] Date of Patent: Dec. 10, 1991

[54] PROCESS FOR PREPARING PARA-HYDROXYBENZOIC ACID

[75] Inventors: Toshinoub Suzuki; Makiko Ijiri; Tokio Iizuka; Tadahiro Wakui, all of Chiba, Japan

[73] Assignee: Kawasaki Steel Corp., Hyogo, Japan

[21] Appl. No.: 368,320

[22] PCT Filed: Oct. 15, 1988

[86] PCT No.: PCT/JP88/01051

§ 371 Date: Jun. 14, 1989

§ 102(e) Date: Jun. 14, 1989

[87] PCT Pub. No.: WO89/03379

PCT Pub. Date: Apr. 20, 1989

[30] Foreign Application Priority Data

Oct. 16, 1987 [JP] Japan .................................. 62-262213
Jul. 12, 1988 [JP] Japan .................................. 63-173084

[51] Int. Cl.$^5$ ............................................. C07C 51/15
[52] U.S. Cl. ...................................... 562/424; 562/423
[58] Field of Search ................................. 562/424, 423

[56] References Cited

U.S. PATENT DOCUMENTS

| | | | |
|---|---|---|---|
| 4,032,555 | 6/1977 | Bottaccio et al. | 558/303 |
| 4,034,006 | 7/1977 | Lind et al. | 562/424 |
| 4,036,873 | 7/1977 | Huffman | 562/424 |
| 4,072,707 | 2/1978 | Grosso | 562/424 |
| 4,508,920 | 4/1985 | Stopp et al. | 562/424 |
| 4,529,817 | 7/1985 | Stopp et al. | 562/424 |

FOREIGN PATENT DOCUMENTS

| | | |
|---|---|---|
| 298289 | 1/1989 | European Pat. Off. |
| 2922340 | 12/1980 | Fed. Rep. of Germany |
| 1189385 | 4/1970 | United Kingdom |

*Primary Examiner*—Paul J. Killos
*Attorney, Agent, or Firm*—Bierman and Muserlian

[57] ABSTRACT

Para-hydroxybenzoic acid is prepared by reacting an alkali metal salt of phenol except the lithium and sodium salts with carbon dioxide in the presence of at least one compound selected from compounds of the following formulae (I) and (II):

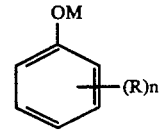

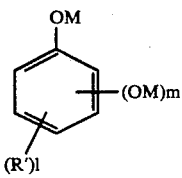

In formulae (I) and (II), M is an alkali metal except lithium and sodium; R is any substituent except an aliphatic hydroxy group having up to 4 carbon atoms, an aliphatic mercapto group having up to 4 carbon atoms, a substituent having at least one of them as its structural unit, and a hydrogen atom; R' is any substituent except an aliphatic hydroxy group having up to 4 carbon atoms, an aliphatic mercapto group having up to 4 carbon atoms, and a substituent having at least one of them as its structural unit; in formula (I) n is an integer of 1 to 5, and R groups may be the same or different when n is more than one; in formula (II) m is an integer of 1 to 5 and l in an integer of 0 to 4, and M alkali metals may be the same or different when m is one or more, and R' groups may be the same or different when l is more than one. The reaction may be carried out in the presence or absence of reaction medium.

11 Claims, No Drawings

PROCESS FOR PREPARING PARA-HYDROXYBENZOIC ACID

BACKGROUND OF THE INVENTION

This invention relates to a process for preparing para-hydroxybenzoic acid using the Kolbe-Schmitt process.

Para-hydroxybenzoic acid finds a wide variety of applications as starting material for polymeric materials. Particularly in these days, it draws attention as starting material for liquid crystalline polyesters having high strength and high heat resistance. Also alkyl esters of para-hydroxybenzoic acid are useful as antimolds for cosmetics and industrial materials.

Industrial preparation of para-hydroxybenzoic acid in the prior art is by solid-gas phase reaction involving reacting powdered potassium phenolate with carbon dioxide at elevated temperatures under pressure which is known as the Kolbe-Schmitt process.

As is well known from the past, the Kolbe-Schmitt reaction is to react an alkali phenolate with carbon dioxide at elevated temperatures under pressure. The use of sodium phenolate as the reactant results in salicylic acid and the use of potassium phenolate predominantly results in para-hydroxybenzoic acid. In fact, a number of patents were issued on the preparation of para-hydroxybenzoic acid utilizing such solid-gas phase reaction.

Many of these preparation processes succeeded in preparing salicylic acid in as high yields as about 90%. As to para-hydroxybenzoic acid, however, all the processes available as far can prepare the end product in yields of at most 50%. In recent years, it was proposed to use various inert reaction media.

To name a few, the recently proposed methods use aprotic polar solvents (Japanese Patent Publication No. 29942/1968), aromatic hydrocarbons and aromatic ethers (Japanese Patent Publication Nos. 1617/1966 and 30063/1975), diaryls, diaryl alkanes, triaryl alkanes or hydrogenated ones thereof (Japanese Patent Application Kokai No. 164751/1984), and kerosine or gas oil (Japanese Patent Publication No. 12185/1977), producing para-hydroxybenzoic acid in a yield of 44%, 47%, 54%, 78% and 53%, respectively.

In contrast, salicylic acid can often be produced by reaction using a reaction medium in high yields of about 90% as in the case of solid-gas phase reaction.

Improvements in these methods were made by the co-existence of phenol in the reaction system as proposed in Japanese Patent Publication No. 37658/1975, Japanese Patent Application Kokai No. 115053/1986, and Japanese Patent Publication No. 9529/1970, which report a para-hydroxybenzoic acid yield of 64%, 78% and 75%, respectively.

These improved methods, however, are essentially mere modifications of the type of reaction medium or limitations of reaction conditions. They are not yet regarded high in the percent yield of para-hydroxybenzoic acid produced which is of primary importance in the synthetic chemical industry.

Therefore, an object of the present invention is to provide a process for preparing in high yields para-hydroxybenzoic acid which finds a wide variety of applications as the starting material for various polymeric materials.

SUMMARY OF THE INVENTION

The above object is achieved by the present invention as defined below.

According to the present invention, there is provided a process for preparing para-hydroxybenzoic acid, comprising reacting an alkali metal salt of phenol except the lithium and sodium salts with carbon dioxide in the presence of at least one compound selected from compounds of the following formulae (I) and (II):

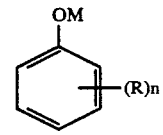

I

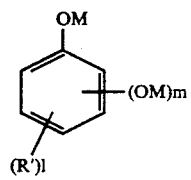

II

In formulae (I) and (II), M is an alkali metal except lithium and sodium.

In formula (I), R is any substituent except an aliphatic hydroxy group having up to 4 carbon atoms, an aliphatic mercapto group having up to 4 carbon atoms, a substituent having at least one of them as its structural unit, and a hydrogen atom.

In formula (II), R' is any substituent except an aliphatic hydroxy group having up to 4 carbon atoms, an aliphatic mercapto group having up to 4 carbon atoms, and a substituent having at least one of them as its structural unit.

In formula (I), n is an integer of 1 to 5, and R groups may be the same or different when n is more than one.

In formula (II), m is an integer of 1 to 5 and l is an integer of 0 to 4, and M alkali metals may be the same or different when m is one or more, and R' groups may be the same or different when l is more than one.

Preferably, the alkali metal salt of phenol is potassium phenolate, and the compound of formula (I) and/or (II) is a potassium salt.

Preferably, the compound of formula (I) is potassium mono-, di- and/or tri-substituted phenolate.

preferably, the alkali metal salt or phenol is potassium phenolate, and a mixture of the potassium phenolate and the potassium salt of compound of formula (I) and/or (II) is obtained from tar acid or cresol acid which is a mixture of phenol and substituted phenols.

The reaction may be carried out in the presence or absence of an inert medium.

BEST MODE FOR CARRYING OUT THE INVENTION

The invention will be illustrated in detail.

According to the present invention, an alkali metal salt of phenol except the lithium and sodium salts is reacted with carbon dioxide in the presence of a compound of formula (I) and/or (II).

Formula (I) representing the compound used herein is shown below.

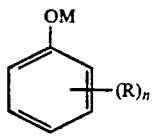

(I)

In formula (I), R is any substituent except an aliphatic hydroxy group having up to 4 carbon atoms, an aliphatic mercapto group having up to 4 carbon atoms, a substituent having at least one of them as its structural unit, and a hydrogen atom. Examples of the substituent represented by R include alkyl groups, alkenyl groups, alkynyl groups, alkoxy groups, amino groups, imino groups, halogen atoms, (aromatic) hydroxy groups, nitro groups and phenyl groups. These groups except halogen atoms may be substituted ones or a mixture of such radicals insofar as the above-mentioned requirement on R is met. Their examples include an isopropyl group, aminoalkyl group, alkylaminoalkyl group, dialkylaminoalkyl group, acylamino group, halogenated alkyl group, nitroalkyl group, phenylalkyl group, methoxy group, alkylamino group, dialkylamino group, acyl group, styryl group, alkylphenyl group, alkoxyphenyl group, aminophenyl group, halogenated phenyl group, hydroxyphenyl group, and nitrophenyl group.

Preferred substituents in formula (I) are electron donative groups, for example, alkyl groups such as methyl and alkoxy groups such as methoxy although phenyl and similar groups are also preferred.

Formula (II) representing the compound used herein is shown below.

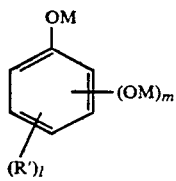

(II)

In formula (II), R' includes those groups defined for R and a hydrogen atom.

Preferred substituents in formula (II) are electron donative groups, for example, alkyl groups such as methyl and alkoxy groups such as methoxy although a hydrogen atom, phenyl and similar groups are also preferred.

In the practice of the present invention, the alkali metal of the alkali metal phenolates and M in the compounds of formula (I) and/or (II) are selected from K, Rb, Cs and Fr, and may be the same or different, but preferably the same, with K being especially preferred for economical reasons.

The process of the present invention may be either reaction in the absence of a reaction medium or reaction in the presence of an inert reaction medium, and allows para-hydroxybenzoic acid to form in high yields without using a reaction medium. The present process is advantageous with respect to agitation even in the absence of a reaction medium as well as in the presence of a reaction medium, as compared with the prior art solid-gas phase reaction, since a reaction mixture or starting composition of the present process becomes liquid due to melting point depression at a reaction temperature above the mixed melting point of the reaction mixture. The present process is very convenient in that para-hydroxybenzoic acid is produced in high yields since the compound of formula (I) and/or (II) is converted to a corresponding liquid or low-melting substituted phenol with the progress of reaction.

The mixed melting point of the reaction mixture may be used as a measure for determining whether the process of the present invention is carried out in the presence or absence of a reaction medium.

The amount of the compound of formula (I) and/or (II) coexisting in the reaction mixture may be in the range of from 0.2 to 30 equivalents, preferably from 0.5 to 10 equivalents, more preferably from 0.8 to 3 equivalents, calculated as the equivalent of the alkali metal oxy group of the compound based on the equivalent of the reactant, potassium phenolate, rubidium phenolate, cesium phenolate or francium phenolate.

When the reactant used is potassium phenolate and the compound of formula (II) used is the dipotassium salt of dihydroxybenzene, for example, the amount of the latter coexisting in the reaction mixture may be in the range of from 0.1 to 15 moles, preferably from 0.25 to 5 moles, more preferably 0.4 to 1.5 moles per mole of the former as calculated on a molar basis, but may be determined by taking into account the mixed melting point of the mixture particularly when reaction is carried out in the absence of a reaction medium.

The present process also has an advantage that at the end of reaction, all or most of the compound of formula (I) and/or (II) may be recovered as such and/or as free substituted phenols for reuse.

In the practice of the present invention, the reaction temperature may be at least 100° C., preferably 200° to 500° C., and the pressure of carbon dioxide may range from atmospheric pressure to 50 kg/cm$^2$ (G), preferably from atmospheric pressure to 15 kg/cm$^2$ (G).

The carbon dioxide used herein may be diluted or mixed with a gas which is inert to the reactant and product under reaction conditions as specified herein. For example, carbon dioxide may be introduced in admixture with nitrogen, hydrogen, helium, argon, carbon monoxide, hydrocarbons, or the like. Blast furnace gases resulting from an iron making plant as by-products may also be used with an economic advantage since carbon dioxide is contained therein. When such a carbon dioxide gas mixture is used, the partial pressure of carbon dioxide may range from atmospheric pressure to 50 kg/cm$^2$ (G), preferably from atmospheric pressure to 15 kg/cm$^2$ (G).

Preferred examples of the compounds of formula (I) as defined above are given below.

Preferred compounds of formula (I) are potassium mono-substituted phenolates, in which the substituent may be at an ortho, meta or para position, with illustrative examples including potassium cresolate and potassium phenylphenolate or potassium salt of hydroxybiphenyl.

Also preferred are corresponding cesium mono-substituted phenolates and rubidium mono-substituted phenolates.

Preferred compounds of formula (I) are potassium di-substituted phenolates, in which two substituent positions may be in any combination, with illustrative examples including potassium 2,3-, 2,4-, 2,5-, 2,6-, 3,4- and 3,5-xylenols.

Preferred compounds of formula (I) are potassium tri-substituted phenolates, in which three substituent positions may be in any combination. Inter alia, potassium 2,4,6-tri-substituted phenolates are preferred because they are inert to carbonation, with illustrative examples including potassium 2,4,6-trimethylphenolate.

The amount of the potassium substituted-phenolate used may be determined within the above-mentioned range by taking into account the equivalents of potassium oxy group relative to the potassium phenolate and the mixed melting point.

Other reaction conditions including reaction temperature and carbon dioxide pressure may be appropriately selected within the above-mentioned ranges.

Examples of the compound of formula (II) include the dipotassium salt of dihydroxybenzene as mentioned above and various other salts.

The compounds of formula (I) and/or (II) may be used alone or in admixture of two or more.

In the practice of the present invention, the potassium salt of phenol and the potassium salt of compound of formula (I) and/or (II) may be obtained from tar acid or cresol acid which is available from coal tar or the like as a mixture of phenol and substituted phenols. Such tar acids or cresol acids are inexpensive and form the mixture contemplated herein so that they are best suited for the process of the present invention. It is preferred to convert tar acids or cresol acids into potassium salts if they are used.

The use of rubidium or cesium salts is also contemplated herein.

The process of the present invention may be carried out in either a batchwise or continuous manner or in a combined manner although continuous operation is preferred with industrial advantages.

The process of the present invention may be carried out in an inert reaction medium, examples of which include aromatic hydrocarbons, aromatic ethers, aromatic alkanes, aromatic alkenes, aromatic ketones, and hydrogenated products thereof, aliphatic petroleum hydrocarbons, aprotic polar solvents, and higher alcohols. These reaction media may be used alone or as a mixture of two or more. Illustrative examples include biphenyl, terphenyl, naphthalene, anthracene, ditolylethane, dibenzyltoluene, methylnaphthalene, isopropylnaphthalene, GS 250 (a mixture of aromatic compounds containing methylnaphthalene as a main ingredient), NeoSK oil (available from Soken Chemical K.K.), Dowtherm (a mixture of diphenyl and diphenylether), ethylbiphenyl, diphenyl ether, hydrogenated terphenyl, benzophenone, kerosene and/or gas oil having a boiling point of at least 150° C., N,N-dimethylformamide, N,N-dimethylacetamide, dimethylsulfoxide, hexamethylphosphoramide, higher alcohols having 5 to 15 carbon atoms, and a mixture thereof. Preferred are those media in which potassium phenolate and the compound of formula (I) and/or (II) are not soluble, which are insoluble in water, and which are liquid at a temperature of at least 100° C., more conveniently liquid at a temperature above room temperature, and more preferably have a boiling point of at least 200° C.

Illustrative examples are gas oil having a boiling point of at least 250° C., NeoSK-oil, Dowtherm, and isopropylnaphthalene.

The use of these media has an additional advantage of ease of control of reaction pressure.

In order that reaction be carried out in a continuous manner in a reaction medium, the reaction medium may be selected by taking into account its melting point, fluidity and solubility of free phenols.

The reaction system may be agitated independent of whether the reaction medium is present or absent. Higher speed rotation and/or more vigorous shaking is preferred to promote contact between reactants, and turbulent flow inducing conditions are more preferred.

The potassium phenolate and the compound of formula (I) and/or (II) used herein are preferably in powder form. A smaller particle size or less than about 300 μm is preferred for both the compounds. The particle size is an important factor for the reaction in the absence of a reaction medium.

The process of the present invention can produce para-hydroxybenzoic acid in higher yields than the prior art conventional processes.

Examples and comparative examples are given below to illustrate the present invention. In the following examples and comparative examples, quantitative determination was by chromatography.

EXAMPLE 1

A pressure vessel was charged with 6.59 grams of potassium phenolate and 7.30 grams of potassium para-cresolate both in dry powder form, and 25 grams of NeoSK-1400 (a dibenzyltoluene mixture medium produced by Soken Chemical K.K.). With stirring at 1,000 r.p.m., reaction was carried out at a carbon dioxide pressure of 7 kg/cm$^2$ (G) and 300° C. for one hour.

An analysis of the product at the end of reaction showed a para-hydroxybenzoic acid yield of 88.4% (6.09 grams) on the basis of the potassium phenolate.

EXAMPLE 2

A pressure vessel was charged with 15.28 grams of an equimolar mixture of powdered potassium phenolate and powder potassium 2,4,6-trimethylphenolate and 24.7 grams of NeoSK-1400. With stirring at 1,000 r.p.m., reaction was carried out at a carbon dioxide pressure of 7 kg/cm$^2$ (G) and 230° C. for one hour.

An analysis of the product at the end of reaction showed a para-hydroxybenzoic acid yield of 82.3% on the basis of the potassium phenolate.

EXAMPLE 3

A pressure vessel was charged with 6.69 grams of potassium phenolate and 8.95 grams of potassium 2,4,6-trimethylphenolate both in dry powder form, and 25.0 grams of gas oil having a boiling point in the range of 250° to 340° C. With stirring at 1,000 r.p.m., reaction was carried out at a carbon dioxide pressure of 11 kg/cm$^2$ (G) and 230° C. for one hour.

An analysis of the product at the end of reaction showed a para-hydroxybenzoic acid yield of 84.6% on the basis of the potassium phenolate.

EXAMPLE 4

A cresol acid was used which was a mixture of phenol and substituted phenols obtained from coal tar. Potassium hydroxide was added to cresylic acid to form dry potassium cresylic acid, which was analyzed to be a mixture of, on a weight percent basis, 44.68% of potassium phenolate, 12.99% of potassium ortho-cresolate, 25.44% of potassium meta-cresolate, and 13.47% of potassium para-cresolate, the remainder 3.42% consisting mainly of potassium xylenolates.

A pressure vessel was charged with 10.24 grams of the powdered potassium cresolates and 25 ml of NeoSK-1400. With stirring at 1,000 r.p.m., reaction was carried out at a carbon dioxide pressure of 7 kg/cm$^2$(G) and 250° C. for 3 hours.

An analysis of the product at the end of reaction showed a para-hydroxybenzoic acid yield of 89.9% on the basis of the potassium phenolate.

EXAMPLE 5

A tar acid was used which was a mixture of phenol and substituted phenols obtained from coal tar. Potassium hydroxide was added to tar acid to form dry potassium tar acid, which was analyzed to be a mixture of, on a weight percent basis, 41.15% of potassium phenolate, 9.55% of potassium ortho-cresolate, 17.61% of potassium meta-cresolate, 9.13% of potassium para-cresolate, and 8.95% of potassium xylenolates, the remainder 13.61% being unknown impurities probably inherent to the tar acid.

A pressure vessel was charged with 13.60 grams of the powdered potassium salt of the tar acid and 25 grams of NeoSK-1400. With stirring at 1,000 r.p.m., reaction was carried out at a carbon dioxide pressure of 7 kg/cm$^2$ (G) and 270° C. for one hour.

An analysis of the product at the end of reaction showed a para-hydroxybenzoic acid yield of 81.5% on the basis of the potassium phenolate.

EXAMPLE 6

A pressure vessel was charged with 6.76 grams of potassium phenolate, 7.54% grams of potassium ortho-cresolate, and 25 grams of NeoSK-1400. With stirring at 1,000 r.p.m., reaction was carried out at a carbon dioxide pressure of 7 kg/cm$^2$ (G) and 300° C. for one hour.

An analysis of the product at the end of reaction showed a para-hydroxybenzoic acid yield of 83.6% on the basis of the potassium phenolate.

EXAMPLE 7

A pressure vessel was charged with 6.98 grams of potassium phenolate, 7.54 grams of potassium meta-cresolate, and 25 grams of NeoSK-1400. Reaction was carried out in the same manner as in Example 6.

An analysis of the product at the end of reaction showed a para-hydroxybenzoic acid yield of 80.0% on the basis of the potassium phenolate.

EXAMPLES 8 to 13

Reaction was carried out by charging a pressure vessel with 6.6 grams of potassium phenolate, 8.0 grams of a potassium xylenolate, and 25 grams of NeoSK-1400. The results are shown in the following Table.

| Example | Potassium xylenolate | Reaction temp. (°C.) | Carbon dioxide pressure kg/cm$^2$, G) | Reaction time (hr.) | P-hydroxybenzoic acid yield (%) |
|---|---|---|---|---|---|
| 8 | potassium 2,3-xylenolate | 300 | 7 | 1 | 81.8 |
| 9 | potassium 2,4-xylenolate | 310 | 7 | 1 | 84.5 |
| 10 | potassium 2,5-xylenolate | 280 | 10 | 1 | 74.8 |
| 11 | potassium 2,6-xylenolate | 230 | 7 | 1 | 85.6 |
| 12 | potassium 3,4-xylenolate | 300 | 7 | 0.5 | 88.3 |
| 13 | potassium 3,5-xylenolate | 260 | 7 | 1 | 87.7 |

EXAMPLE 14

A pressure vessel was charged with 6.63 grams of potassium phenolate, 10.98 grams of potassium ortho-phenylphenolate, and 25 grams of NeoSK-1400. With stirring at 1,000 r.p.m., reaction was carried out at a carbon dioxide pressure of 7 kg/cm$^2$(G) and 300° C. for one hour.

An analysis of the product at the end of reaction showed a para-hydroxybenzoic acid yield of 77.8% on the basis of the potassium phenolate.

EXAMPLE 15

A pressure vessel was charged with 6.60 grams of potassium phenolate, 10.96 grams of potassium meta-phenylphenolate, and 25 grams of NeoSK-1400. Reaction was carried out in the same manner as in Example 14.

An analysis of the product at the end of reaction showed a para-hydroxybenzoic acid yield of 78.5% on the basis of the potassium phenolate.

EXAMPLE 16

A pressure vessel was charged with 17.79 grams of an equimolar mixture of rubidium phenolate and rubidium para-cresolate, and 25 grams of NeoSK-1400. With stirring at 1,000 r.p.m., reaction was carried out at a carbon dioxide pressure of 3 kg/cm$^2$(G) and 300° C. for one hour.

An analysis of the product at the end of reaction showed a para-hydroxybenzoic acid yield of 81.3% on the basis of the rubidium phenolate.

EXAMPLE 17

A pressure vessel was charged with 27.60 grams of an equimolar mixture of cesium phenolate and cesium para-cresolate, and 25 grams of NeoSK-1400. Reaction was carried out in the same manner as in Example 16.

An analysis of the product at the end of reaction showed a para-hydroxybenzoic acid yield of 62.2% on the basis of the cesium phenolate.

EXAMPLE 18

A pressure vessel was charged with 6.65 grams of potassium phenolate and 7.40 grams of potassium ortho-cresolate both in dry powder form. With stirring, reaction was carried out at a carbon dioxide pressure of 7 kg/cm$^2$ (G) and 220° to 240° C. for ten minutes. The equimolar mixture of potassium phenolate and potassium ortho-cresolate has a eutectic point of 209° C. in peak value as measured by differential thermal analysis (same throughout the examples). An analysis of the product at the end of reaction showed a para-hydroxybenzoic acid yield of 79.6% on the basis of the potassium phenolate.

EXAMPLE 19

A tar acid was used which was a mixture of phenol and substituted phenols obtained from coal tar.

Potassium hydroxide was added to tar acid to form dry potassium tar acid, which was analyzed to be a mixture of, on a weight percent basis, 40.96% of potassium phenolate, 9.66% of potassium ortho-cresolate, 17.82% of potassium meta-cresolate, 9.23% of potassium para-cresolate, and 9.19% of potassium xylenolates, the remainder 13.14% being unknown impurities probably inherent to the tar acid and containing traces of thiophenols. The potassium salt of the tar acid had a mixed melting point of about 230° C.

A pressure vessel was charged with 15.03 grams of the powdered potassium salt of the tar acid. With stirring, reaction was carried out at a carbon dioxide pressure of 8 kg/cm² (G) and 250° to 260° C. for one hour. An analysis of the product at the end of reaction showed a para-hydroxybenzoic acid yield of 71.1% on the basis of the potassium phenolate.

COMPARATIVE EXAMPLE 1

A pressure vessel was charged with 6.60 grams of potassium phenolate and 26.4 grams of NeoSK-1400. With stirring at 1,000 r.p.m., reaction was carried out at a carbon dioxide pressure of 7 kg/cm² (G) and 230° C. for 20 minutes.

An analysis of the product at the end of reaction showed a para-hydroxybenzoic acid yield of 45.1% on the basis of the potassium phenolate.

COMPARATIVE EXAMPLE 2

A pressure vessel was charged with 6.59 grams of potassium phenolate, 2.36 grams of phenol, and 26.5 grams of NeoSK-1400. Reaction was carried out under the same conditions as in Comparative Example 1. An analysis of the product at the end of reaction showed a para-hydroxybenzoic acid yield of 47.3% on the basis of the potassium phenolate.

COMPARATIVE EXAMPLE 3

A pressure vessel was charged with 6.83 grams of potassium phenolate, 7.30 grams of 2,4,6-trimethylphenol, and 25.5 grams of NeoSK-1400. Reaction was carried out under the same conditions as in Comparative Example 1.

An analysis of the product at the end of reaction showed a para-hydroxybenzoic acid yield of 46.8% on the basis of the potassium phenolate.

INDUSTRIAL APPLICABILITY

According to the present invention, para-hydroxybenzoic acid can be produced in high yields and high purity.

The present invention thus allows para-hydroxybenzoic acid to find a wider range of use as starting material for polymeric materials and pharmaceutical and agricultural compositions.

We claim:

1. A process for preparing para-hydroxybenzoic acid, comprising reacting an alkali metal salt of phenol with carbon dioxide in the presence of at least one compound selected from compounds of the following formulae (I) and (II):

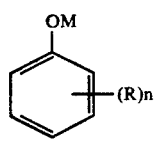

I

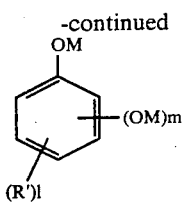

II wherein M is an alkali metal the alkali metal of the phenolate and M being individually selected from the group consisting of potassium, cesium, rubium and francium in formula (I) R is any organic substituent except an aliphatic hydroxy group having up to 4 carbon atoms, an aliphatic mercapto group having up to 4 carbon atoms, and a substituent having at least one of them as its structural unit, and a hydrogen atom;

in formula (II), R' is any substituent except an aliphatic hydroxy group having up to 4 carbon atoms, an aliphatic mercapto group having up to 4 carbon atoms, and a substituent having at least one of them as its structural unit;

in formula (I) R' is an integer of 1 to 5, and R groups may be the same or different when n is more then one;

in formula (II) m is an integer of 1 to 5 and l is an integer of 0 to 4, and M alkali metals may be the same or different when m is one or more, and R' groups may be the same or different when l is more than one.

2. A process for preparing para-hydroxybenzoic acid according to claim 1 wherein said alkali metal salt of phenol is potassium phenolate.

3. A process for preparing para-hydroxybenzoic acid according to claim 1 wherein said compound of formula (I) and/or (II) is a potassium salt.

4. A process for preparing para-hydroxybenzoic acid according to claim 1 wherein said compound of formula (I) is potassium mono-, di- and/or tri-substituted phenolate.

5. A process for preparing para-hydroxybenzoic acid according to claim 1 wherein said alkali metal salt of phenol is potassium phenolate, and a mixture of said potassium phenolate and the potassium salt of compound of formula (I) and/or (II) is obtained from tar acid or cresol acid which is a mixture of phenol and substituted phenols.

6. A process for preparing para-hydroxybenzoic acid according to claim 1 wherein the reaction is carried out in an inert medium.

7. A process for preparing para-hydroxybenzoic acid according to claim 1 wherein the reaction is carried out in the absence of a reaction medium.

8. A process for preparing para-hydroxybenzoic acid according to claim 2 wherein said compound of formula I and/or II is a potassium salt.

9. A process for preparing para-hydroxybenzoic acid according to claim 2 wherein said compound of formula I is potassium mono-,di- and/or tri-substituted phenolate.

10. A process of claim 1 wherein R is selected from the group consisting of alkyl, alkenyl, alkynyl, alkoxy, —NH₂, =NH, halogen, —NO₂, phenyl, hydroxy phenyl, nitro phenyl, alkylphenyl, alkylamino, dialkylamino, alkoxy phenyl and acyl.

11. A process of claim 1 wherein R' is selected from the group consisting of hydrogen, alkyl, alkenyl, alkynyl, alkoxy, —NH₂, =NH, halogen, —NO₂, phenyl, hydroxy phenyl, nitro phenyl, alkylphenyl, alkylamino, dialkylamino, alkoxy phenyl and acyl.

* * * * *